United States Patent
Busson et al.

(10) Patent No.: US 12,083,127 B2
(45) Date of Patent: Sep. 10, 2024

(54) PHARMACEUTICAL FORMULATION

(71) Applicant: Hoffmann-La Roche Inc., Little Falls, NJ (US)

(72) Inventors: Patrick Busson, Badenweiler-Lipburg (DE); Georg Hummel, Rheinweiler (DE); Thomas Peter Wilhelm Knobloch, Wallbach (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/295,670

(22) Filed: Apr. 4, 2023

(65) Prior Publication Data

US 2023/0390302 A1     Dec. 7, 2023

Related U.S. Application Data

(63) Continuation of application No. 16/894,345, filed on Jun. 5, 2020, now abandoned, which is a continuation of application No. PCT/EP2018/083772, filed on Dec. 6, 2018.

(30) Foreign Application Priority Data

Dec. 8, 2017 (EP) .................... 17206197

(51) Int. Cl.
*A61K 31/551* (2006.01)
*A61K 9/16* (2006.01)
*A61K 9/28* (2006.01)
*A61K 9/50* (2006.01)

(52) U.S. Cl.
CPC .......... *A61K 31/551* (2013.01); *A61K 9/1611* (2013.01); *A61K 9/1617* (2013.01); *A61K 9/1623* (2013.01); *A61K 9/1652* (2013.01); *A61K 9/2893* (2013.01); *A61K 9/501* (2013.01); *A61K 9/5026* (2013.01); *A61K 9/5031* (2013.01)

(58) Field of Classification Search
CPC .. A61K 31/551; A61K 9/1611; A61K 9/1617; A61K 9/1623; A61K 9/1652; A61K 9/2893; A61K 9/501; A61K 9/5026; A61K 9/5031
See application file for complete search history.

(56) References Cited

U.S. PATENT DOCUMENTS

| | | | |
|---|---|---|---|
| 7,923,028 B2 | 4/2011 | Kaestle et al. | |
| 2006/0083785 A1 | 4/2006 | Kerrish et al. | |
| 2011/0263578 A1 | 10/2011 | Dolente et al. | |
| 2021/0228490 A1 | 7/2021 | Maurer et al. | |

FOREIGN PATENT DOCUMENTS

| | | |
|---|---|---|
| CN | 102216304 A | 10/2011 |
| CN | 102227428 A | 10/2011 |
| CN | 105793263 A | 7/2016 |
| WO | 2010/057795 A1 | 5/2010 |
| WO | 2010/060836 A1 | 6/2010 |
| WO | 2015/024819 A1 | 2/2015 |
| WO | 2015/082370 A1 | 6/2015 |

OTHER PUBLICATIONS

Osherovich, L.,, "Building tools against autism" Science-Business eXchange 5(16):1-2 (Apr. 19, 2012).
"International Preliminary Report on Patentability—PCT/EP2018/083772" (Report Issuance Date: Jun. 9, 2020),:pp. 1-7 (Jun. 18, 2020).
"International Search Report—PCT/EP2018/083772":pp. 1-5 (Feb. 25, 2019).
"Pediatric dysphagia and rehabilitation—Intravenous enteral feeding" CVision Technologies 27(5):29-34 ( 2012).
Pharm Eur Tablets_Monograph_Nov. 2016, Jan. 2014:0478.
USP General Information Pharmaceutical Dosage Forms_Nov. 2016, pp. 1445-1468.

*Primary Examiner* — Jessica Worsham
(74) *Attorney, Agent, or Firm* — Robert C. Hall

(57) ABSTRACT

The invention relates to a stable, peroxide-free pharmaceutical composition of 8-chloro-5-methyl-1-[4-(2-pyridyloxy) cyclohexyl]-4,6-dihydro-[1,2,4]triazolo[4,3-a][1,4]benzodiazepine, and a process for the preparation thereof and its use in the treatment of diseases or conditions in which V1a inhibition plays a role or is implicated, such as autism spectrum disorder (ASD), and the core social and communication deficits of patients associated therewith. The formulation includes a compressed tablet kernel comprising: (a) compound of formula I,

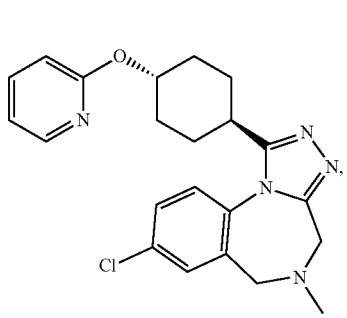

disintegrant, filler, glidant and lubricant; and (b) a film coating system comprising coating agent, colorant, plasticizer, anti-tacking agent, and coating vehicle. The process for making the formulation comprises combining the tablet kernel ingredients into a blend, sieving the blend, and compressing the blend to form a tablet kernel, and spraying the film coating system onto the tablet kernels.

3 Claims, 1 Drawing Sheet

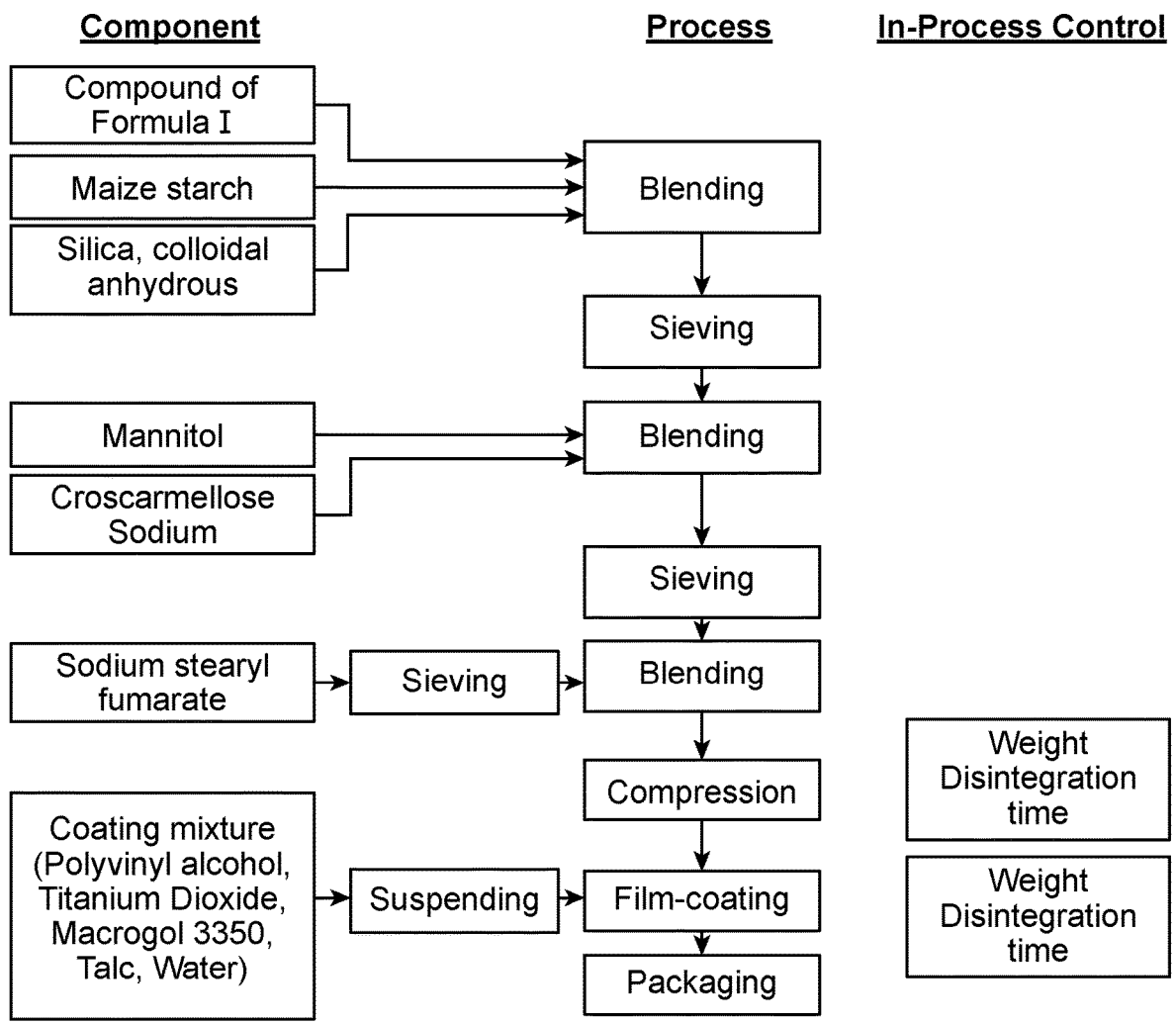

PHARMACEUTICAL FORMULATION

CROSS REFERENCE TO RELATED APPLICATIONS

This application is a continuation of U.S. application Ser. Ser. No. 16/894,345 filed on Jun. 5, 2020, which is a continuation of PCT/EP2018/083772 filed on Dec. 6, 2018, which claims the benefit of EP application No. 17206197.0 filed on Dec. 8, 2017, the disclosures of which are incorporated herein by reference.

FIELD OF THE INVENTION

Present invention relates to a pharmaceutical composition comprising 8-chloro-5-methyl-1-[4-(2-pyridyloxy)cyclohexyl]-4,6-dihydro-[1,2,4]triazolo[4,3-a][1,4]benzodiazepine, a process for the preparation thereof and its use in the treatment of diseases.

BACKGROUND OF THE INVENTION

A variety of chemical compounds have been reported for the treatment or prevention of a disease or condition in which V1a inhibition plays a role or is implicated.

8-chloro-5-methyl-1-[4-(2-pyridyloxy)cyclohexyl]-4,6-dihydro-[1,2,4]triazolo[4,3-a][1,4]benzodiazepine (CAS 1228088-30-9) has been described in WO 2010/060836[1], and its complex polymorphism landscape as well as ways to its syntheses are described in WO 2015/082370[2].

8-chloro-5-methyl-1-[4-(2-pyridyloxy)cyclohexyl]-4,6-dihydro [1,2,4]triazolo[4,3-a][1,4]benzodiazepine is useful in the treatment of autism, in particular in the treatment of the core social and communication deficits of patients with autism spectrum disorder (ASD), while currently available treatments address only associated behavioral problems or comorbidities.

Previously known formulations of 8-chloro-5-methyl-1-[4-(2-pyridyloxy)cyclohexyl]-4,6-dihydro-[1,2,4]triazolo[4,3-a][1,4]benzodiazepine were capsule formulations containing lactose monohydrate and binders that had peroxides as impurities. Further, the capsule formulation was made using a fluid bed granulation process.

Lactose-free formulations are interesting to cope with potential lactose intolerances in patients. Peroxid-free formulations, such as povidone-free formulations, are interesting to stabilize 8-chloro-5-methyl-1-[4-(2-pyridyloxy)cyclohexyl]-4,6-dihydro-[1,2,4]triazolo[4,3-a][1,4]benzodiazepine and avoid its oxidation to 8-chloro-5-methyl-5-oxido-1-[4-(2-pyridyloxy)cyclohexyl]-4,6-dihydro-[1,2,4]triazolo[4,3-a][1,4]benzodiazepin-5-ium.

Administering and managing medications is a daily task of a caregiver, i.e. of an adult for a child patient. More effective modes of drug administration benefit patient and caregiver, and will thus improve compliance and reduced caregiver stress, substantiated by greater satisfaction and less interference with daily life. 8-chloro-5-methyl-1-[4-(2-pyridyloxy)cyclohexyl]-4,6-dihydro-[1,2,4]triazolo[4,3-a][1,4]benzodiazepine coming in a capsule is difficult to swallow at a whole for child patients. Removing powdered 8-chloro-5-methyl-1-[4-(2-pyridyloxy)cyclohexyl]-4,6-dihydro-[1,2,4]triazolo[4,3-a][1,4]benzodiazepine from the capsule to mix the drug with food or beverage before administration to a patient does expose the caregiver to the possibility to get drug on the skin, nose or moth, or breath in the powder.

The fluid bed granulation technique under wet conditions might induce an undesired change in the polymorphic form of 8-chloro-5-methyl-1-[4-(2-pyridyloxy)cyclohexyl]-4,6-dihydro-[1,2,4]triazolo[4,3-a][1,4]benzodiazepine. The fluid bed granulation technique is a sensitive (humidity, temperature, air) and complex process, limited e.g. by batch and filter seize.

There is thus a need for a broadly applicable and stable pharmaceutical formulation of 8-chloro-5-methyl-1-[4-(2-pyridyloxy)cyclohexyl]-4,6-dihydro-[1,2,4]triazolo[4,3-a][1,4]benzodiazepine, suitable for pediatric and adolescent patients. The formulation should further be able to be produced in an easy and reproducible manner.

SUMMARY OF THE INVENTION

The invention relates to a pharmaceutical composition comprising a compound of formula I,

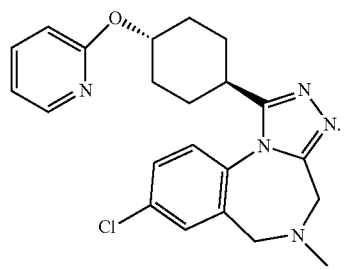

i) The formulation may be peroxide free, and may comprise a disintegrant, a filler, a glidant and a lubricant.

DESCRIPTION OF THE DRAWINGS

FIG. 1 is a flow chart illustrating preparation of the formulations of the invention.

DETAILED DESCRIPTION OF THE INVENTION

All embodiments of present invention can be combined.

Definitions

The term "disintegrant" refers to a substance that is added to aid in the deaggregation of an oral dosage form by e.g. swelling, wicking, producing effervescence or melting. This can be excipients that dissolve and expand when wet causing the tablet to break apart in the body and release the active ingredient for absorption. Examples include crosslinked polymers like crospovidone (like Polyplasdone™ XL10), croscarmellose sodium (like Disolcel®) etc. and modified starches like sodium starch glycolate (like Primojel®). A specific example is Croscarmellose sodium.

The term "filler" refers to excipients that fill out the size of a tablet by increasing the bulk volume. Fillers make it possible for the final product to have the proper volume for patient handling Examples of fillers include cellulose, lactose, starch, mannitol, etc. Specific examples are starch (like STA-RX 1500, CAS No. 9057-07-2), Maize starch, Mannitol (like Parteck® M100, Parteck® M200), Isomalt (like GalenIQ™ 721), maltodextrin (like Maliodextrin DE 15-18) and microcrystalline cellulose (like Avicel® PH 101, Avicel® PH 102). Specific examples are mannitol and maize starch.

The term "binder" refers to excipients that hold the ingredients in a tablet together. Binders ensure that tablets and granules can be formed with required mechanical strength, and give volume to low active dose tablets. Examples of binders include polymers like polyvinlypyrrolidon (PVP, such as copovidone (PVP/VA 64), (Povidone K30), etc.), hydroxypropyl methylcellulose (HPMC), hydroxypropylcellulose (HPC) and proteins like gelatin. A specific example is copovidone.

The term "glidant" refers to excipients that enhance product flow by reducing interparticulate friction. Examples of glidants include silicon dioxide (colloidal), polyethylene glycol PEG 6000, fumed silicon dioxide Aerosil® 200, talc and the like. A specific example is silica, colloidal anhydrous.

The term "lubricant" refers to excipients that prevent ingredients from clumping together and from sticking to the tablet punches or capsule filling machine. Lubricants also ensure that tablet formation and ejection can occur with low friction between active ingredient and wall. Examples of lubricants are minerals like talc or silica and fats like stearin, magnesium stearate, sodium stearyl fumarate, etc. A specific example is sodium stearyl fumarate.

The term "Film Coating System" refers to a system coating the kernel. Examples of film coating systems include Opadry®-based material and the like. The term "Opadry®-based material" refers to a "Film Coating System" like Opadry® II 31F265002 brown, Opadry® 32F265006 brown, Opadry® II 31K28690 white, Opadry® QX 321A265005 brown, Opadry® II 85F26792 brown, Opadry® II 85F18422 white, Opadry® II 85E205106 blue, Opadry® 85F220063 yellow etc.

The term "Coating Agent" refers to a material suitable as thin coat applied to a solid dosage form like a tablet. An example is Polyvinyl alcohol.

The term "colourant" refers to a colour changing agent like a white pigment. Examples are titanium dioxide and aluminum (2E)-3-oxo-2-(3-oxo-5-sulfo-1H-indol-2-ylidene)-1H-indole-5-sulfonic acid.

The term "plasticizer" refers to additives that decrease the plasticity or viscosity of a material. An example is Macrogol/PEG 3350.

The term "sweetener" refers to additives that sweeten the composition. An example is sucralose.

The term "anti-tacking agent" is a component in a coating system to prevent tackiness of the dosage forms during the manufacturing process. Examples are talc, glyceryl monostearate, magnesium stearate, silicon dioxide, and the like. A specific example is talc.

The term "coating vehicle" or "processing liquid" refers to a material that helps adding the coating to the kernel. The coating vehicle is essentially removed during processing. Examples are organic solvents, water, and the like. A specific example is purified water.

A term like x±y % means the range from x %–y % to x %+y %. An example is 5±1% means the range from 4% (incl.) to 6% (incl.).

A term like "x±y % by weight" in context with any disintegrant, filler, glidant, lubricant and/or the compound of formula I refers to "x±y % by weight" of the kernel's total weight. For example 10 mg of the compound of formula I in a tablet kernel of 200 mg is 5% by weight of the compound of formula I of the total Kernel weight.

A term like "x±y % by weight" in context with any coating agent, colourant, plasticizer and/or anti-tacking agent refers to "x±y % by weight" of the film coating's total weight. For example 1.5 mg titanium dioxide in the tablet's coating of 6 mg is 25% by weight of the total weight of the "film coating system" or "coating system".

The term" comprising the compound of formula I in a kernel" means that the compound of formula I is only in the kernel.

The term "pharmaceutically acceptable excipient" refers to carriers and auxiliary substances such as diluents, fillers, glidants, lubricants and the like that are compatible with the other ingredients of the formulation.

The terms "dispersible tablet" or "tablet for oral dispersion USP" refers to uncoated tablets or film-coated tablets intended to be dispersed in liquid such as water, milk and the like giving a homogeneous dispersion before administration to the patients. A dispersible tablet has several advantages over the granule formulation, like it is also suitable for use in newborns (age 0-6 months), it can be dispersed in milk, breast milk especially and are easy to use which minimizes the risk of application errors by health professionals or parents. Dispersible tablets have low physical resistance and are more sensitive to moisture and may degrade at higher humidity conditions. It is therefore of interest to have dispersible tablets which ensure conservation of the active ingredient until its release[3].

The term "lactose-free" refers to a pharmaceutical composition that does not contain lactose. Lactose-free formulations are interesting to cope with potential lactose intolerances in patients.

The term "peroxide-free" refers to a pharmaceutical composition that does not contain any peroxides. 8-chloro-5-methyl-1-[4-(2-pyridyloxy)cyclohexyl]-4,6-dihydro-[1,2,4]triazolo[4,3-a][1,4]benzodiazepine might oxidize to 8-chloro-5-methyl-5-oxido-1-[4-(2-pyridyloxy)cyclohexyl]-4,6-dihydro-[1,2,4]triazolo[4,3-a][1,4]benzodiazepin-5-ium in the presence of a peroxide.

Polymorph F of the compound of formula I is described in detail in WO 2015/082370[2], claims 4-5, page 28 lines 22-24 and FIGS. 16-18. Form H of the compound of formula I is described in detail in WO 2015/082370[2], claim 16, page 29 lines 1-6 and FIGS. 22-23.

The compound of formula I can be used in as a very fine powder, which might be difficult to process in fluid-bed granulation due to loss of compound of formula I in the manufacturing process.

Present invention relates to a pharmaceutical composition comprising a compound of formula I,

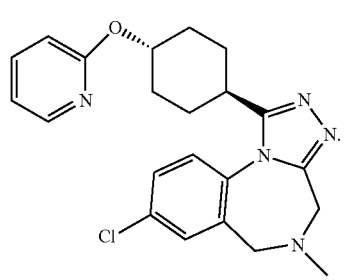

I

E1: A specific embodiment of present invention relates to a pharmaceutical composition consisting of the compound of formula I as active ingredient and pharmaceutically acceptable excipients.

E2: A specific embodiment of present invention relates to a peroxide-free pharmaceutical composition comprising the compound of formula I.

E3: A specific embodiment of present invention relates to a peroxide-free pharmaceutical composition consisting of the compound of formula I and pharmaceutically acceptable excipients.

E4: A specific embodiment of present invention relates to a lactose-free pharmaceutical composition comprising of the compound of formula I as active ingredient and pharmaceutically acceptable excipients.

E5: A specific embodiment of present invention relates to a lactose-free pharmaceutical composition consisting of the compound of formula I as active ingredient and pharmaceutically acceptable excipients.

E6: A specific embodiment of present invention relates to the pharmaceutical composition as described herein, comprising the compound of formula I in a kernel optionally wherein the Kernel is being coated by a film coating system, in particular 5±1% weight of the compound of formula I, more particular 5% by weight of the compound of formula I, or 2.5±1% weight of the compound of formula I, more particular 2.5% by weight of the compound of formula I.

E7: A specific embodiment of present invention relates to the pharmaceutical composition as described herein, comprising the compound of formula I in a coated kernel, in particular 5±1% by weight of the compound of formula I, more particular 5% by weight of the compound of formula I, or 2.5±1% by weight of the compound of formula I, more particular 2.5% by weight of the compound of formula I.

E8: A specific embodiment of present invention relates to the pharmaceutical composition as described herein, comprising the compound of formula I in a kernel.

E9: A specific embodiment of present invention relates to the pharmaceutical composition as described herein, comprising the compound of formula I in a coated kernel.

E10: A specific embodiment of present invention relates to the pharmaceutical composition as described herein, consisting of the compound of formula I in a kernel.

E11: A specific embodiment of present invention relates to the pharmaceutical composition as described herein, consisting of the compound of formula I in a coated kernel.

E12: A specific embodiment of present invention relates to the pharmaceutical composition as described herein, comprising 5.25±4.75% by weight of the compound of formula I in a kernel, in particular in a coated kernel.

E13: A specific embodiment of present invention relates to the pharmaceutical composition as described herein, comprising 5±1% by weight of the compound of formula I in a kernel.

E14: A specific embodiment of present invention relates to the pharmaceutical composition as described herein, comprising 5±1% by weight of the compound of formula I in a coated kernel.

E15: A specific embodiment of present invention relates to the pharmaceutical composition as described herein, consisting of 5±1% by weight of the compound of formula I in a kernel and pharmaceutically acceptable excipients.

E16: A specific embodiment of present invention relates to the pharmaceutical composition as described herein, consisting of 5±1% by weight of the compound of formula I in a coated kernel and pharmaceutically acceptable excipients.

E17: A specific embodiment of present invention relates to the pharmaceutical composition as described herein, comprising 5% by weight of the compound of formula I in a kernel.

E18: A specific embodiment of present invention relates to the pharmaceutical composition as described herein, comprising 5% by weight of the compound of formula I in a coated kernel.

E19: A specific embodiment of present invention relates to the pharmaceutical composition as described herein, consisting of 5% by weight of the compound of formula I in a kernel and pharmaceutically acceptable excipients.

E20: A specific embodiment of present invention relates to the pharmaceutical composition as described herein, consisting of 5% by weight of the compound of formula I in a coated kernel and pharmaceutically acceptable excipients.

E21: A specific embodiment of present invention relates to the pharmaceutical composition as described herein, comprising 2.5±1% by weight of the compound of formula I in a kernel.

E22: A specific embodiment of present invention relates to the pharmaceutical composition as described herein, comprising 2.5±1% by weight of the compound of formula I in a coated kernel.

E23: A specific embodiment of present invention relates to the pharmaceutical composition as described herein, further comprising at least one of the following compounds:
i) disintegrant,
ii) filler,
iii) glidant and
iv) lubricant.

E24: A specific embodiment of present invention relates to the pharmaceutical composition as described herein, further comprising the following compounds
i) disintegrant,
ii) filler,
iii) glidant and
iv) lubricant.

E25: A specific embodiment of present invention relates to the pharmaceutical composition as described herein, further comprising at least one of the following compounds in the kernel:
i) disintegrant,
ii) filler,
iii) glidant and
iv) lubricant.

E26: A specific embodiment of present invention relates to the pharmaceutical composition as described herein, further comprising the following compounds in the coated kernel
i) disintegrant,
ii) filler,
iii) glidant and
iv) lubricant.

E27: A specific embodiment of present invention relates to the pharmaceutical composition as described herein further comprising a sweetener, in particular sucralose, more particular 1% by weight of the kernel, in the kernel, in particular in the coated kernel.

E28: A specific embodiment of present invention relates to the pharmaceutical composition as described herein, wherein
i) the disintegrant is croscarmellose sodium, in particular 5±1% by weight croscarmellose sodium, more particular 5% by weight croscarmellose sodium,
ii) the filler is mannitol and/or starch, in particular 85±3% by weight filler, more particular 70% by weight mannitol and 15% by weight starch,
iii) the glidant is colloidal anhydrous silica, in particular 2±1% by weight colloidal anhydrous silica, more particular 2% by weight colloidal anhydrous silica, and iv) the lubricant is sodium stearyl fumarate, in particular 3±1% by weight sodium stearyl fumarate, more particular 3% by weight sodium stearyl fumarate.

E29: A specific embodiment of present invention relates to the pharmaceutical composition as described herein, wherein the disintegrant is croscarmellose sodium, in particular 5±1% by weight croscarmellose sodium, more particular 5% by weight croscarmellose sodium.

E30: A specific embodiment of present invention relates to the pharmaceutical composition as described herein, wherein the disintegrant is sodium carboxymethylstarch, in particular 7.5±2.5% by weight sodium carboxymethylstarch.

E31: A specific embodiment of present invention relates to the pharmaceutical composition as described herein, wherein the disintegrant is croscarmellose sodium.

E32: A specific embodiment of present invention relates to the pharmaceutical composition as described herein, wherein the disintegrant is 7.5±2.5% by weight croscarmellose sodium E33: A specific embodiment of present invention relates to the pharmaceutical composition as described herein, wherein the disintegrant is 5±1% by weight croscarmellose sodium.

E34: A specific embodiment of present invention relates to the pharmaceutical composition as described herein, wherein the disintegrant is 5% by weight croscarmellose sodium.

E35: A specific embodiment of present invention relates to the pharmaceutical composition as described herein, wherein a filler is mannitol, in particular 60±20% by weight mannitol.

E36: A specific embodiment of present invention relates to the pharmaceutical composition as described herein, wherein a filler is isomalt, in particular 75% by weight isomalt.

E37: A specific embodiment of present invention relates to the pharmaceutical composition as described herein, wherein a filler is starch, in particular 15±10% by weight starch.

E38: A specific embodiment of present invention relates to the pharmaceutical composition as described herein, wherein a filler is microcrystalline cellulose, in particular 25±10% by weight microcrystalline cellulose.

E39: A specific embodiment of present invention relates to the pharmaceutical composition as described herein, wherein a filler is maltodextrin, in particular 5% by weight maltodextrin.

E40: A specific embodiment of present invention relates to the pharmaceutical composition as described herein, wherein the filler is mannitol and/or starch, in particular 85±3% by weight filler, more particular 70% by weight mannitol and 15% by weight starch.

E41: A specific embodiment of present invention relates to the pharmaceutical composition as described herein, wherein the filler is mannitol and starch, in particular 85±3% by weight mannitol and starch, more particular 70% by weight mannitol and 15% by weight starch.

E42: A specific embodiment of present invention relates to the pharmaceutical composition as described herein, wherein the filler is 85±3% by weight mannitol and starch.

E43: A specific embodiment of present invention relates to the pharmaceutical composition as described herein, wherein the filler is 70% by weight mannitol and 15% by weight starch.

E44: A specific embodiment of present invention relates to the pharmaceutical composition as described herein, wherein the filler is 72.5% by weight mannitol and 15% by weight starch.

E45: A specific embodiment of present invention relates to the pharmaceutical composition as described herein, wherein the glidant is colloidal anhydrous silica, in particular 2±1% by weight colloidal anhydrous silica, more particular 2% by weight colloidal anhydrous silica.

E46: A specific embodiment of present invention relates to the pharmaceutical composition as described herein, wherein the glidant is colloidal anhydrous silica, in particular 2±1% by weight colloidal anhydrous silica, more particular 2% by weight colloidal anhydrous silica.

E47: A specific embodiment of present invention relates to the pharmaceutical composition as described herein, wherein the glidant is colloidal anhydrous silica.

E48: A specific embodiment of present invention relates to the pharmaceutical composition as described herein, wherein the glidant is 1.75±1.25% by weight colloidal anhydrous silica.

E49: A specific embodiment of present invention relates to the pharmaceutical composition as described herein, wherein the glidant is 2±1% by weight colloidal anhydrous silica.

E50: A specific embodiment of present invention relates to the pharmaceutical composition as described herein, wherein the glidant is 2% by weight colloidal anhydrous silica.

E51: A specific embodiment of present invention relates to the pharmaceutical composition as described herein, wherein the lubricant is sodium stearyl fumarate, in particular 3±1% by weight sodium stearyl fumarate, more particular 3% by weight sodium stearyl fumarate.

E52: A specific embodiment of present invention relates to the pharmaceutical composition as described herein, wherein the lubricant is sodium stearyl fumarate.

E53: A specific embodiment of present invention relates to the pharmaceutical composition as described herein, wherein the lubricant is 3±1% by weight sodium stearyl fumarate.

E54: A specific embodiment of present invention relates to the pharmaceutical composition as described herein, wherein the lubricant is 3% by weight sodium stearyl fumarate.

E55: A specific embodiment of present invention relates to the pharmaceutical composition as described herein, further comprising a film coating system, in particular wherein a film coating system comprising
   i) a coating agent,
   ii) a colourant,
   iii) a plasticizer,
   iv) an anti-tacking agent, and
   v) a coating vehicle.

E56: A specific embodiment of present invention relates to the pharmaceutical composition as described herein, further comprising a film coating system, in particular wherein the film coating system comprises:
   i) a coating agent,
   ii) a colourant,
   iii) a plasticizer,
   iv) an anti-tacking agent, and
   v) a coating vehicle.

E57: A specific embodiment of present invention relates to the pharmaceutical composition as described herein, further consisting of a film coating system, in particular a film coating system comprising
- i) a coating agent,
- ii) a colourant,
- iii) a plasticizer,
- iv) an anti-tacking agent, and
- v) a coating vehicle.

E58: A specific embodiment of present invention relates to the pharmaceutical composition as described herein, further consisting of a film coating system, in particular wherein the film coating system comprises:
- i) a coating agent,
- ii) a colourant,
- iii) a plasticizer,
- iv) an anti-tacking agent, and
- v) a coating vehicle.

E59: A specific embodiment of present invention relates to the pharmaceutical composition as described herein, further consisting of a film coating system, in particular a film coating system consisting of
- i) a coating agent,
- ii) a colourant,
- iii) a plasticizer,
- iv) an anti-tacking agent, and
- v) a coating vehicle.

E60: A specific embodiment of present invention relates to the pharmaceutical composition as described herein, further consisting of a film coating system, in particular the film coating system consists of
- i) a coating agent,
- ii) a colourant,
- iii) a plasticizer,
- iv) an anti-tacking agent, and
- v) a coating vehicle.

E61: A specific embodiment of present invention relates to the pharmaceutical composition as described herein, wherein
- i) the coating agent is polyvinyl alcohol, in particular 40±2% by weight polyvinyl alcohol, more particular 40% by weight polyvinyl alcohol,
- ii) the colourant is titanium dioxide, in particular 25±2% by weight titanium dioxide, more particular 25% by weight titanium dioxide,
- iii) the plasticizer is Macrogol/PEG 3350, in particular 20.2±2% by weight Macrogol/PEG 3350, more particular 20.2% by weight Macrogol/PEG 3350,
- iv) the anti-tacking agent is talc, in particular 14.8±1% by weight talc, more particular 14.8% by weight talc, and
- v) the coating vehicle is purified water.

E62: A specific embodiment of present invention relates to the pharmaceutical composition as described herein, wherein
- i) the coating agent is polyvinyl alcohol, in particular 40±2% by weight polyvinyl alcohol, more particular 40% by weight polyvinyl alcohol,
- ii) the first colourant is titanium dioxide, in particular 23±2% by weight titanium dioxide, more particular 22.8% by weight titanium dioxide,
- iii) the second colourant is aluminum (2E)-3-oxo-2-(3-oxo-5-sulfo-1H-indol-2-ylidene)-1H-indole-5-sulfonic acid, in particular 2±1% by weight (2E)-3-oxo-2-(3-oxo-5-sulfo-1H-indol-2-ylidene)-1H-indole-5-sulfonic acid, more particular 2.2% by weight (2E)-3-oxo-2-(3-oxo-5-sulfo-1H-indol-2-ylidene)-1H-indole-5-sulfonic acid,
- iv) the plasticizer is Macrogol/PEG 3350, in particular 20.2±2% by weight Macrogol/PEG 3350, more particular 20.2% by weight Macrogol/PEG 3350,
- v) the anti-tacking agent is talc, in particular 14.8±1% by weight talc, more particular 14.8% by weight talc, and
- vi) the coating vehicle is purified water.

E63: A specific embodiment of present invention relates to the pharmaceutical composition as described herein, wherein the coating agent is polyvinyl alcohol, in particular 40±2% by weight polyvinyl alcohol, more particular 40% by weight polyvinyl alcohol.

E64: A specific embodiment of present invention relates to the pharmaceutical composition as described herein, wherein the coating agent is polyvinyl alcohol.

E65: A specific embodiment of present invention relates to the pharmaceutical composition as described herein, wherein the coating agent is 40±2% by weight polyvinyl alcohol.

E66: A specific embodiment of present invention relates to the pharmaceutical composition as described herein, wherein the coating agent is 40% by weight polyvinyl alcohol.

E67: A specific embodiment of present invention relates to the pharmaceutical composition as described herein, wherein the colourant is titanium dioxide/aluminum (2E)-3-oxo-2-(3-oxo-5-sulfo-1H-indol-2-ylidene)-1H-indole-5-sulfonic acid, in particular 25±2% by weight titanium dioxide/aluminum (2E)-3-oxo-2-(3-oxo-5-sulfo-1H-indol-2-ylidene)-1H-indole-5-sulfonic acid, more particular 25% by weight titanium dioxide/aluminum (2E)-3-oxo-2-(3-oxo-5-sulfo-1H-indol-2-ylidene)-1H-indole-5-sulfonic acid.

E68: A specific embodiment of present invention relates to the pharmaceutical composition as described herein, wherein the film coating system comprises:
- i) the coating agent is polyvinyl alcohol, in particular 40±2% by weight polyvinyl alcohol, more particular 40% by weight polyvinyl alcohol,
- ii) the colourant is titanium dioxide, in particular 25±2% by weight titanium dioxide, more particular 25% by weight titanium dioxide,
- iii) the plasticizer is Macrogol/PEG 3350, in particular 20.2±2% by weight Macrogol/PEG 3350, more particular 20.2% by weight Macrogol/PEG 3350,
- iv) the anti-tacking agent is talc, in particular 14.8±1% by weight talc, more particular 14.8% by weight talc, and
- v) the coating vehicle is purified water.

E69: A specific embodiment of present invention relates to the pharmaceutical composition as described herein, wherein the film coating system comprises:
- i) the coating agent is polyvinyl alcohol, in particular 40±2% by weight polyvinyl alcohol, more particular 40% by weight polyvinyl alcohol,
- ii) the first colourant is titanium dioxide, in particular 23±2% by weight titanium dioxide, more particular 22.8% by weight titanium dioxide,
- iii) the second colourant is aluminum (2E)-3-oxo-2-(3-oxo-5-sulfo-1H-indol-2-ylidene)-1H-indole-5-sulfonic acid, in particular 2±1% by weight (2E)-3-oxo-2-(3-oxo-5-sulfo-1H-indol-2-ylidene)-1H-indole-5-sulfonic acid, more particular 2.2% by weight (2E)-3-oxo-2-(3-oxo-5-sulfo-1H-indol-2-ylidene)-1H-indole-5-sulfonic acid,
- iv) the plasticizer is Macrogol/PEG 3350, in particular 20.2±2% by weight Macrogol/PEG 3350, more particular 20.2% by weight Macrogol/PEG 3350,
- v) the anti-tacking agent is talc, in particular 14.8±1% by weight talc, more particular 14.8% by weight talc, and
- vi) the coating vehicle is purified water.

E70: The pharmaceutical composition as described herein, comprising an Opadry®-based material as film coating system of the kernel.

E71: A specific embodiment of present invention relates to the pharmaceutical composition as described herein which is

| Kernel | mg |
| --- | --- |
| a compound of formula I | 10.00 |
| Mannitol | 140 |
| Maize Starch | 30 |
| Croscarmellose Sodium | 10 |
| Silica, Colloidal Anhydrous | 4 |
| Sodium Stearyl Fumarate | 6 |
| Film Coating System | |
| Polyvinyl Alcohol | 2.40 |
| Titanium Dioxide/Aluminum (2E)-3-oxo-2-(3-oxo-5-sulfo-1H-indol-2-ylidene)-1H-indole-5-sulfonic acid | 1.3692/0.1308 |
| Macrogol/PEG 3350 | 1.21 |
| Talc | 0.89 |

E72: A specific embodiment of present invention relates to a process to produce the pharmaceutical composition as described herein, in particular a process comprising the following steps
  i) blend the compound of formula I, maize starch, colloidal anhydrous silica in Container 1,
  ii) sieve blend the mixture of i) having a screen size approximately 1.5 mm into Container 2,
  iii) add mannitol and croscarmellose sodium to Container 2 and blend
  iv) sieve blend the mixture of iii) having a screen size approximately 1.5 mm into Container 1
  v) add pre-sieved sodium stearyl fumarate having a screen size approximately 0.5 mm into Container 1 and blend,
  vi) compress the blend of v) into tablet kernels, and
  vii) prepare the film-coating system, and
  viii) spray it onto the kernels.

E73: A specific embodiment of present invention relates to a process to produce the pharmaceutical composition as described herein, in particular a process consisting of the following steps
  i) blend the compound of formula I, maize starch, colloidal anhydrous silica in Container 1,
  ii) sieve blend the mixture of i) having a screen size approximately 1.5 mm into Container 2,
  iii) add mannitol and croscarmellose sodium to Container 2 and blend
  iv) sieve blend the mixture of iii) having a screen size approximately 1.5 mm into Container 1
  v) add pre-sieved sodium stearyl fumarate having a screen size approximately 0.5 mm into Container 1 and blend,
  vi) compress the blend of v) into tablet kernels, and
  vii) prepare the film-coating system, and
  viii) spray it onto the kernels.

E74: A specific embodiment of present invention relates to a process as described in FIG. 1 to produce the pharmaceutical composition as described herein.

E75: A specific embodiment of present invention relates to the pharmaceutical composition as described herein for use in the treatment of autism.

E76: A specific embodiment of present invention relates to the pharmaceutical composition as described herein for use in the treatment of ASD.

E77: A specific embodiment of present invention relates to the pharmaceutical composition as described herein for use in the treatment of the core social and communication deficits of patients with autism spectrum disorder.

E78: A specific embodiment of present invention relates to a method of treatment autism, which method comprises administering the pharmaceutical composition as described herein.

E79: A specific embodiment of present invention relates to a method of treatment ASD, which method comprises administering the pharmaceutical composition as described herein.

E80: A specific embodiment of present invention relates to a method of treatment of the core social and communication deficits of patients with autism spectrum disorder, which method comprises administering the pharmaceutical composition as described herein.

E81: A specific embodiment of present invention relates to a use of the pharmaceutical composition as described herein for the treatment of ASD.

E82: A specific embodiment of present invention relates to a use of the pharmaceutical composition as described herein for the treatment of autism.

E83: A specific embodiment of present invention relates to a use of the pharmaceutical composition as described herein for the treatment of the core social and communication deficits of patients with autism spectrum disorder.

E84: A specific embodiment of present invention relates to a kit comprising the pharmaceutical composition as described herein and prescribing information also known as "leaflet".

E85: A specific embodiment of present invention relates to a tablet comprising a pharmaceutical composition as described herein.

E86: A specific embodiment of present invention relates to a tablet consisting of a pharmaceutical composition as described herein.

E87: A specific embodiment of present invention relates to a pharmaceutical composition as described herein for oral administration.

E88: A specific embodiment of present invention relates to a dispersible tablet comprising a compound of formula I.

E89: A specific embodiment of present invention relates to a dispersible tablet comprising the pharmaceutical composition as described herein.

E90: A specific embodiment of present invention relates to a dispersible tablet consisting of the pharmaceutical composition as described herein.

E91: A specific embodiment of present invention relates to a dispersible tablet as described herein that disintegrates within 3 minutes using water at 15-25° C.

E92: A specific embodiment of present invention relates to a process as described herein which uses direct compression of the kernel as described herein. Direct compression is the preferred technology as it minimizes the risk of polymorphic changes of the compound of formula I and the tablets produced with direct compression show good disintegration results.

E93: A specific embodiment of present invention relates to the pharmaceutical composition as described herein, comprising the compound of formula I in a coated kernel, in particular 2.5±1% by weight of the compound of formula I, more particular 2.5% by weight of the compound of formula I.

E94: A specific embodiment of present invention relates to the pharmaceutical composition as described herein, wherein the filler is mannitol and/or starch, in particular 87.5±3% by weight filler, more particular 72.5% by weight mannitol and 15% by weight starch.

E95: A specific embodiment of present invention relates to a direct compression process.

E96: A specific embodiment of present invention relates to a pharmaceutical composition consisting of polymorph F of the compound of formula I as active ingredient and pharmaceutically acceptable excipients.

E97: A specific embodiment of present invention relates to a pharmaceutical composition comprising polymorph F of the compound of formula I as active ingredient and pharmaceutically acceptable excipients, substantially free of Form H of the compound of formula I.

E98: A specific embodiment of present invention relates to a pharmaceutical composition consisting of polymorph F of the compound of formula I as active ingredient and pharmaceutically acceptable excipients.

E99: The pharmaceutical composition as described herein, wherein the kernel as described herein is film coated with a 3% by weight of a film coating system as described herein based on the kernel's weight.

E100: The pharmaceutical composition as described herein, wherein the kernel of 200 mg as described herein is film coated 6 mg of a film coating system as described.

E101: The pharmaceutical composition as described herein, that has a disintegration time of more than 180 seconds.

BRIEF DESCRIPTION OF THE FIGURE

FIG. 1: A manufacturing process of a pharmaceutical composition as described herein.

EXPERIMENTAL PART

Example 1

10 mg Dispersible Tablet

| Kernel | mg |
|---|---|
| a compound of formula I | 10.00 |
| Mannitol | 140 |
| Maize Starch | 30 |
| Croscarmellose Sodium | 10 |
| Silica, Colloidal Anhydrous | 4 |
| Sodium Stearyl Fumarate | 6 |
| Film Coating System | |
| Polyvinyl Alcohol | 2.40 |
| Titanium Dioxide | 1.50 |
| Macrogol/PEG 3350 | 1.21 |
| Talc | 0.89 |

Example 2

7 mg Dispersible Tablet

| Kernel | mg |
|---|---|
| a compound of formula I | 7.00 |
| Mannitol | 98 |
| Maize Starch | 21 |
| Croscarmellose Sodium | 7 |
| Silica, Colloidal Anhydrous | 2.8 |
| Sodium Stearyl Fumarate | 4.2 |
| Film Coating System | |
| Polyvinyl Alcohol | 1.68 |
| Titanium Dioxide | 1.05 |
| Macrogol/PEG 3350 | 0.85 |
| Talc | 0.62 |

Example 3

5 mg Dispersible Tablet

| Kernel | mg |
|---|---|
| a compound of formula I | 5.00 |
| Mannitol | 70 |
| Maize Starch | 15 |
| Croscarmellose Sodium | 5 |
| Silica, Colloidal Anhydrous | 2 |
| Sodium Stearyl Fumarate | 3 |
| Film Coating System | |
| Polyvinyl Alcohol | 1.20 |
| Titanium Dioxide | 0.75 |
| Macrogol/PEG 3350 | 0.605 |
| Talc | 0.445 |

Example 4

3 mg Dispersible Tablet

| Kernel | mg |
|---|---|
| a compound of formula I | 3.0 |
| Mannitol | 87.0 |
| Maize Starch | 18.0 |
| Croscarmellose Sodium | 6.0 |
| Silica, Colloidal Anhydrous | 2.4 |
| Sodium Stearyl Fumarate | 3.6 |
| Film Coating System | |
| Polyvinyl Alcohol | 1.44 |
| Titanium Dioxide | 0.90 |
| Macrogol/PEG 3350 | 0.73 |
| Talc | 0.53 |

Example 5

2 mg Dispersible Tablet

| Kernel | mg |
|---|---|
| a compound of formula I | 2.0 |
| Mannitol | 58.0 |
| Maize Starch | 12.0 |
| Croscarmellose Sodium | 4.0 |
| Silica, Colloidal Anhydrous | 1.6 |
| Sodium Stearyl Fumarate | 2.4 |
| Film Coating System | |
| Polyvinyl Alcohol | 0.96 |
| Titanium Dioxide | 0.60 |
| Macrogol/PEG 3350 | 0.48 |
| Talc | 0.36 |

Example 6

1 mg Dispersible Tablet

| Kernel | mg |
|---|---|
| a compound of formula I | 1.0 |
| Mannitol | 62.0 |
| Maize Starch | 13.0 |
| Croscarmellose Sodium | 2.0 |
| Silica, Colloidal Anhydrous | 0.8 |
| Sodium Stearyl Fumarate | 1.2 |
| Film Coating System | |
| Polyvinyl Alcohol | 0.48 |
| Titanium Dioxide | 0.30 |
| Macrogol/PEG 3350 | 0.24 |
| Talc | 0.18 |

Example 7

10 mg Dispersible Tablet

| Kernel | mg |
|---|---|
| a compound of formula I | 10.00 |
| Mannitol | 140 |
| Maize Starch | 30 |
| Croscarmellose Sodium | 10 |
| Silica, Colloidal Anhydrous | 4 |
| Sodium Stearyl Fumarate | 6 |
| Film Coating System | |
| Polyvinyl Alcohol | 2.40 |
| Titanium Dioxide/Aluminum (2E)-3-oxo-2-(3-oxo-5-sulfo-1H-indol-2-ylidene)-1H-indole-5-sulfonic acid | 1.3692/0.1308 |
| Macrogol/PEG 3350 | 1.21 |
| Talc | 0.89 |

Example 8

Disintegration Results of Tablet of Example 1

| Compaction pressure [kN] | Hardness [N] | Disintegration time [s] |
|---|---|---|
| 3 | 70 | 22 |
| 6 | 135 | 67 |
| 9 | 179 | 134 |
| 12 | 189 | 178 |

The direct compression tablets show the advantage of high hardness compared with low disintegration time.

The compaction pressure (=punch force/punch area) is the pressure (in MPa) necessary to form compacts at a pre-determined solid fraction, for example 0.85.

Example 9

Process to Manufacture Tablet of Example 1

1. Add the compound of formula 1, maize starch, silica, and colloidal anhydrous to Blending Container 1 and blend.
2. Sieve blend from Step 1 (screen size approximately 1.5 mm) into Blending Container 2 ("Blend A").
3. Add mannitol and croscarmellose sodium to Blend A in Container 2, and blend.
4. Sieve blend from Step 3 (screen size approximately 1.5 mm) into Blending Container 1 ("Blend B").
5. Add the pre-sieved (screen size approximately 0.5 mm) sodium stearyl fumarate to Blend B and blend ("Final Blend").
6. Compress the Final Blend into tablet cores using a tablet press.
7. Prepare the film-coating suspension using the film-coating mixture and purified water.
8. Spray the film-coating suspension (from Step 7) onto the tablet cores using a pan coater.
9. and optionally package the dispersible tablets.

Example 10

Stability Studies of a Tablet of Example 1

| | Content compound of Formula I mg/unit (by HPLC) | Content degradation products total % (by HPLC) | Shape |
|---|---|---|---|
| Initial analysis | 1.01 | <0.05 | round |
| 30° C./75% RH | | | |
| 1 month | 1.00 | <0.05 | round |
| 3 months | 1.00 | <0.05 | round |
| 40° C./75% RH | | | |
| 1 month | 1.00 | <0.05 | round |
| 3 months | 1.00 | <0.05 | round |

HPLC = high-performance liquid chromatography,
RH = relative humidity

| Dissolution Test after 30 min | Dissolution Data % (RSD) | | | | | |
|---|---|---|---|---|---|---|
| Mean % (RSD) | 3 min | 6 min | 9 min | 12 min | 15 min | 30 min |
| Initial analysis 102 (0.7) | 98 (2.7) | 102 (0.5) | 102 (0.5) | 101 (1.2) | 102 (0.7) | 102 (0.7) |
| 30° C./75% RH | | | | | | |
| 1 month 1.00 (1.4) | 100 (2.2) | 103 (1.9) | 104 (1.8) | 104 (1.6) | 104 (1.5) | 104 (1.4) |
| 3 months 1.00 (0.5) | 94 (1.6) | 99 (0.8) | 100 (0.4) | 100 (0.5) | 100 (0.4) | 100 (0.5) |
| 40° C./75% RH | | | | | | |
| 1 month 1.00 (0.9) | 100 (2.2) | 103 (1.9) | 104 (1.0) | 104 (1.0) | 104 (1.0) | 104 (0.9) |
| 3 months 1.00 (0.7) | 97 (2.0) | 100 (0.9) | 100 (0.9) | 100 (0.8) | 100 (0.7) | 100 (0.7) |

RSD = relative standard deviation
[1] WO 2010/060836
[2] WO 2015/082370
[3] See also Pharm Eur Tablets_Monograph_Nov 2016 and USP General Information Pharmaceutical Dosage Forms_Nov 2016

The invention claimed is:

1. A pharmaceutical composition consisting of a tablet kernel and a film coating system thereon;
the tablet kernel consisting of:
(a) a compound of formula I in an amount of 5% by weight of the tablet kernel;

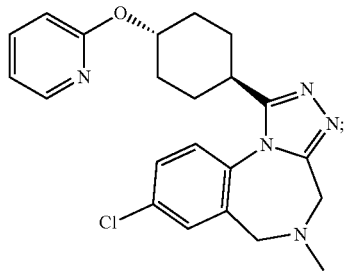

I (b) a disintegrant in an amount of 5% by weight of the tablet kernel wherein the disintegrant is croscarmellose sodium;
(c) a filler wherein the filler is mannitol in an amount of 70% by weight of the tablet kernel and starch in an amount of 15% by weight of the tablet kernel;
(d) a glidant in an amount of 2% by weight of the tablet kernel wherein the glidant is colloidal anhydrous silica; and
(e) a lubricant in an amount of 3% by weight of the tablet kernel wherein the lubricant is sodium stearyl fumarate;
wherein the film coating system consists of:
(i) a coating agent in an amount of 40% by weight of the film coating system wherein the coating agent is polyvinyl alcohol;
(ii) a colorant wherein the colorant is titanium dioxide in an amount of 22.8% by weight of the film coating system and (2E)-3-oxo-2-(3-oxo-5-sulfo-1H-indol-2-ylidene)-1H-indole-5-sulfonic acid in an amount of 2.2% by weight of the film coating system;
(iii) a plasticizer in an amount of 20.2% by weight of the film coating system wherein the plasticizer is Macrogol/PEG 3350;
(iv) an anti-tacking agent in an amount of 14.8% by weight of the film coating system wherein the anti-tacking agent is talc; and
(v) purified water as a coating vehicle.

2. The pharmaceutical composition of claim 1, wherein the film coating system is 3% by weight of the tablet kernel.

3. A process for making the pharmaceutical composition of claim 1, consisting of:
(a) blending the compound of formula I, starch, and colloidal anhydrous silica in a first (a) container;
(b) sieving the resulting blend of (a) using a screen size of approximately 1.5 mm into a second container;
(c) adding the mannitol and croscarmellose sodium to the second container and blending therein;
(d) sieving the resulting blend of (c) with a screen size of approximately 1.5 mm into the first container;
(e) sieving the sodium stearyl fumarate with a screen size approximately 0.5 mm into the first container and blending therein;
(f) compressing the resulting blend of (e) into tablet kernels;
(g) preparing the film-coating system; and
(h) spraying the film coating system onto the tablet kernels.

* * * * *